(12) United States Patent
Xu et al.

(10) Patent No.: US 11,168,063 B2
(45) Date of Patent: Nov. 9, 2021

(54) PREPARATION METHOD FOR ESCITALOPRAM PAMOATE

(71) Applicants: ZHEJIANG HUAHAI PHARMACEUTICAL CO., LTD., Zhejiang (CN); SHANGHAI AOBO PHARMTECH, INC., LTD., Shanghai (CN)

(72) Inventors: Wei Xu, Shanghai (CN); Xi Chen, Shanghai (CN); Hong Gu, Shanghai (CN)

(73) Assignees: Zhejiang Huahai Pharmaceutical Co., Ltd., Zhejiang (CN); Shanghai Aobo Pharmtech, Inc., Ltd., Shanghai (CN)

( * ) Notice: Subject to any disclaimer, the term of this patent is extended or adjusted under 35 U.S.C. 154(b) by 1 day.

(21) Appl. No.: 16/618,898

(22) PCT Filed: Jun. 5, 2018

(86) PCT No.: PCT/CN2018/089996
§ 371 (c)(1),
(2) Date: Dec. 3, 2019

(87) PCT Pub. No.: WO2018/223970
PCT Pub. Date: Dec. 13, 2018

(65) Prior Publication Data
US 2020/0087273 A1    Mar. 19, 2020

(30) Foreign Application Priority Data

Jun. 5, 2017  (CN) .......................... 201710411925.9

(51) Int. Cl.
*C07D 307/87* (2006.01)
(52) U.S. Cl.
CPC .................................. *C07D 307/87* (2013.01)
(58) Field of Classification Search
CPC ..................................................... C07D 307/87
See application file for complete search history.

(56) References Cited

FOREIGN PATENT DOCUMENTS

| CN | 102336729 A | 2/2012 | |
|---|---|---|---|
| CN | 102757414 A | 10/2012 | |
| CN | 104072390 A | 10/2014 | |
| EP | 0 347 066 A1 | 12/1989 | |
| EP | 0347066 B1 * | 3/1995 | ............... A61P 3/04 |
| WO | WO 2018/171589 A1 | 9/2018 | |

OTHER PUBLICATIONS

European Application No. 18813582.6 extended European Search Report dated Feb. 11, 2020 (7 pages).

* cited by examiner

*Primary Examiner* — John S Kenyon
(74) *Attorney, Agent, or Firm* — Alston & Bird LLP

(57) ABSTRACT

The present invention relates to a new preparation method for escitalopram pamoate ((S)-(+)-1-[3-(dimethylamino)propyl]-1-(4-fluorophenyl)-1,3-dihydro-5-cyanoisob enzofuran pamoate), wherein the method is environmentally friendly and pollution-free, and the escitalopram pamoate prepared by means of the method has a high purity and a good repeatability.

6 Claims, 2 Drawing Sheets

PREPARATION METHOD FOR ESCITALOPRAM PAMOATE

This application claims the priority to Chinese Patent Application No. 201710411925.9, with the title of "New Preparation Method For Escitalopram Pamoate", filed on Jun. 5, 2017 before China National Intellectual Property Administration, which is hereby incorporated by reference in its entirety.

FIELD OF THE INVENTION

The present invention relates a new method for preparing escitalopram pamoate, namely ((S)-(+)-1-[3-(dimethylamino)propyl]-1-(4-fluorophenyl)-1,3-dihydro-5 isobenzofurancarbonitrile pamoate, which belongs to the field of chemical medicine.

BACKGROUND OF THE INVENTION

The chemical name of escitalopram is ((S)-(+)-1-[3-(dimethylamino)propyl]-1-(4-fluorophenyl)-1,3-dihydro-5 isobenzofurancarbonitrile. Escitalopram oxalate, jointly developed by Forest Laboratories and Lundbeck, was first launched in Euro-American countries such as Switzerland in March 2002 and was approved by the FDA in August 2002. Escitalopram is a serotonin reuptake inhibitor (SSRI), which has a unique serotonin isotopic site binding mechanism, is highly selective for serotonin receptors and is used in the treatment for major depression and the maintenance treatment for depression.

Patients with major depression are often non-compliant and it is difficult to assess whether the patient has received the exact dose of the drug. Therefore, it is necessary to formulate escitalopram oxalate into a low-solubility salt form with sustained release by means of replacing the acid radical.

Patent EP0347066 discloses escitalopram pamoate and a preparation method thereof. The solvent used was methanol and the starting material was escitalopram and pamoic acid.

Methanol, the solvent used in the above preparation method of escitalopram pamoate, has certain toxicity. Through continuous research, the present inventors have found a new preparation method of escitalopram pamoate by using water as solvent. The method is environmentally friendly and pollution-free, and overcomes the problems of the prior art.

SUMMARY OF THE INVENTION

The present invention provides a method for preparing escitalopram pamoate (compound of formula I).

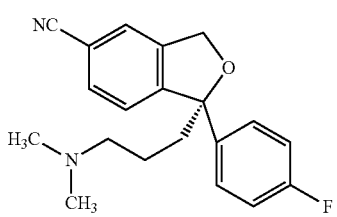

Formula I

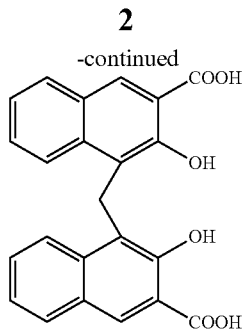

Further, the present invention provides a method for preparing escitalopram pamoate, which comprises dissolving escitalopram oxalate in a solvent and adding a pamoate aqueous solution dropwise to precipitate escitalopram pamoate.

Further, the present invention provides a method for preparing escitalopram pamoate, wherein the solvent is water.

Further, the present invention provides a method for preparing escitalopram pamoate, wherein dissolving is carried out at a temperature of 0-70° C.

Further, the present invention provides a method for preparing escitalopram pamoate, wherein dissolving is carried out at a temperature of 45-65° C.

Further, the present invention provides a method for preparing escitalopram pamoate, wherein the pamoate is pamoate disodium salt.

Furthermore, the present invention provides a method for preparing escitalopram pamoate, wherein the solvent added dropwise is water.

Furthermore, the present invention provides a method for preparing escitalopram pamoate, wherein adding the pamoate aqueous solution dropwise is carried out at a temperature of 0-70° C.

Further, the present invention provides a method for preparing escitalopram pamoate, wherein adding the pamoate aqueous solution dropwise is carried out at a temperature of 45-65° C.

DESCRIPTION OF THE DRAWINGS

In order to more clearly illustrate the examples of the present invention and the technical solutions of the prior art, the following is a brief description of the drawings that need to be used in the examples and the prior art. It is obvious that the drawings in the following description are only some examples of the invention, and other drawings may also be obtained from these drawings by those skilled in the art without any inventive efforts.

DETAILED DESCRIPTION OF THE INVENTION

Figure 1:
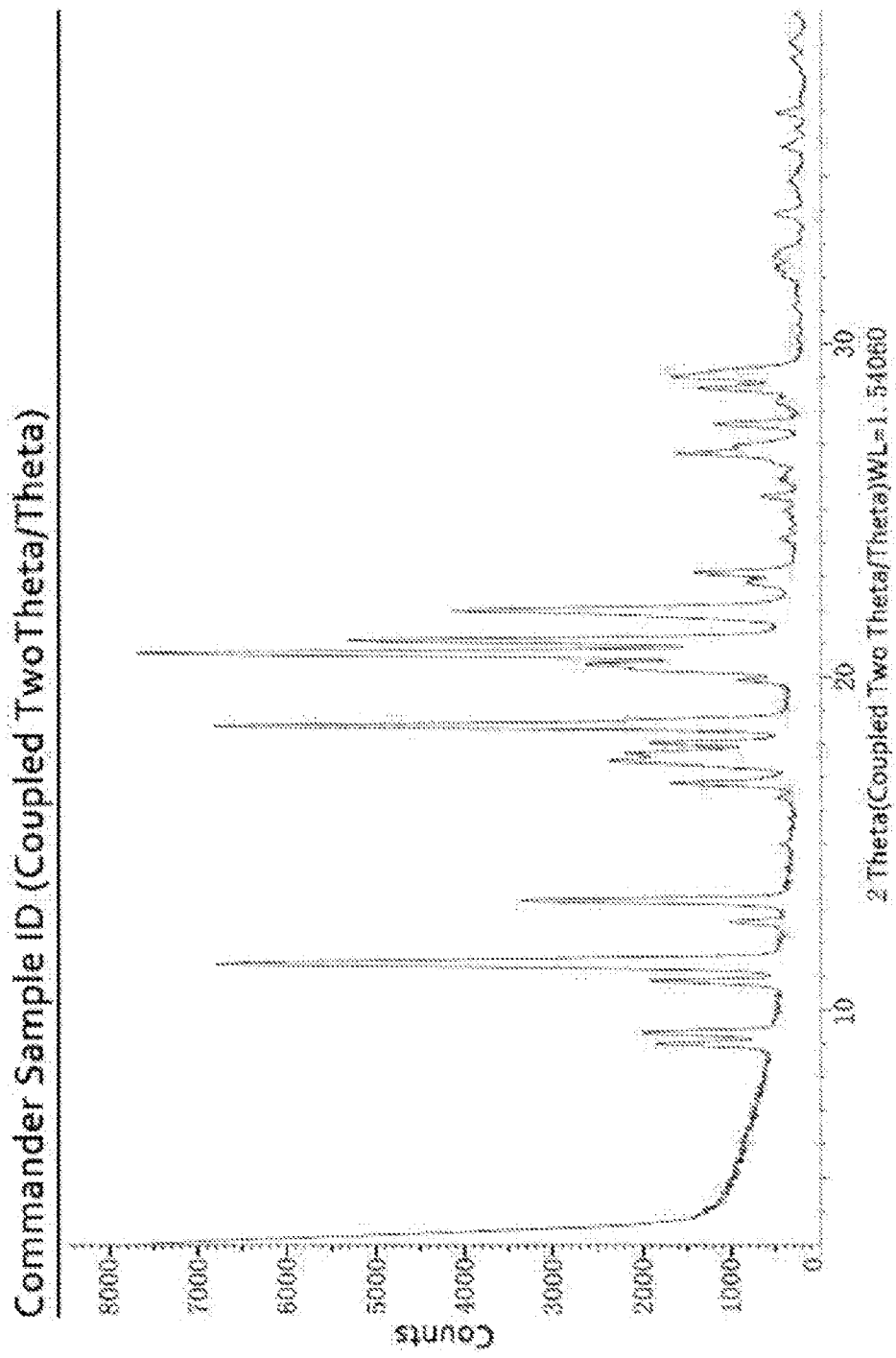
FIG. 1 is an XRPD pattern of escitalopram pamoate.
Figure 2:
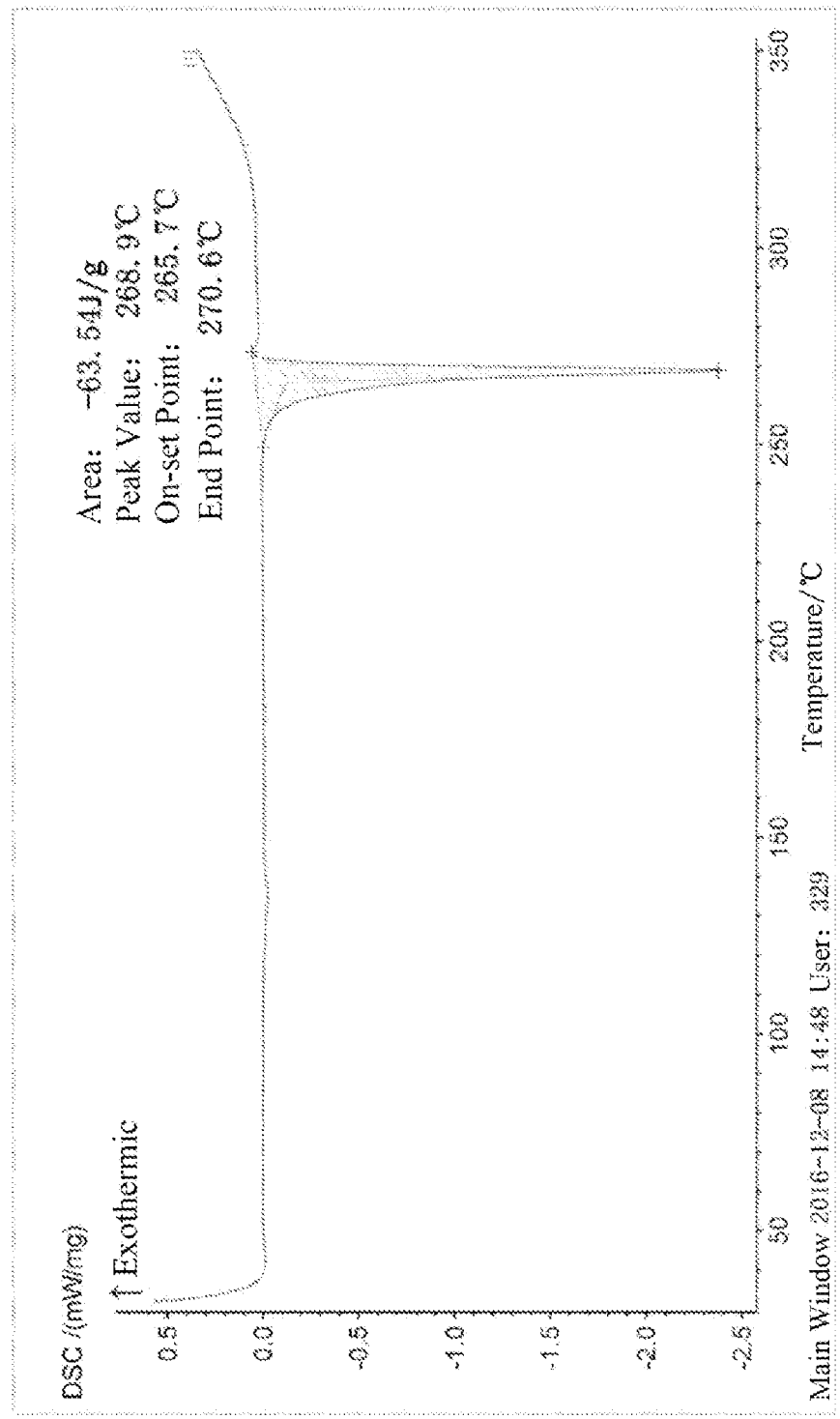
FIG. 2 is a DSC pattern of escitalopram pamoate.

The implementation of the present invention will be described in detail below in combination with the examples. The examples of the present invention include, but are not limited to, the following examples, which should not be construed as limiting the scope of the invention.

The X-ray powder diffraction data of the present invention was measured using BRUKER D8 Advance from Bruker Germany Corporation, with the conditions of voltage and current: 40 kV, 40 mA; goniometer: vertical goniometer, radius 280 mm; slit: DS=2°, SS=1/2°, mask=15 mm, RS=5.0 mm; detector: LYNXEYE detector; scanning mode: continuous scanning; scan range: 3-40°; counting time per step: 0.2 s; total scanning time: 390 s.

The differential scanning calorimetry pattern of the present invention was measured by using DSC 200F3 from NETZSCH Germany Corporation, with a temperature range of 30-350° C. and a heating rate of 10° C./min.

Example 1: Preparation of Escitalopram Pamoate 4 ml of water was added to 500 mg of escitalopram oxalate sample, and was heated to 60° C. to completely dissolve it. 5 ml of water was added to 520 mg of pamoate disodium salt to completely dissolve it at room temperature. The aqueous solution of pamoate disodium salt was added dropwise to the aqueous solution of escitalopram oxalate at 60° C., and a solid appeared immediately with being well dispersed. After the addition was completed, stirring was continued for 2 h and then the reaction mixture was filtered. The filter cake was washed with 50 ml of water, filtered under vacuum for 10 min and dried in vacuo to obtain 850 mg of escitalopram pamoate sample.

Example 2: Preparation of Escitalopram Pamoate 40 ml water was added to 5 g of escitalopram oxalate sample, and was heated to 60° C. to completely dissolve it. 50 ml of water was added to 5.2 g of pamoate disodium salt to completely dissolve it at room temperature. The aqueous solution of pamoate disodium salt was added dropwise to the aqueous solution of escitalopram oxalate at 60° C., and a solid appeared immediately with being well dispersed. After the addition was completed, stirring was continued for 2 h and then the reaction mixture was filtered. The filter cake was washed with 50 ml of water, filtered under vacuum for 10 min and dried in vacuo to obtain 8.5 g of escitalopram pamoate sample.

Example 3: Preparation of Escitalopram Pamoate 400 ml of water was added to 50 g of escitalopram oxalate sample, and was heated to 60° C. to completely dissolve it. 500 ml of water was added to 52 g of pamoate disodium salt to completely dissolve it at room temperature. The aqueous solution of pamoate disodium salt was added dropwise to the aqueous solution of escitalopram oxalate at 60° C., and a solid appeared immediately with being well dispersed. After the addition was completed, stirring was continued for 2 h and then the reaction mixture was filtered. The filter cake was washed with 500 ml of water, filtered under vacuum for 10 min and dried in vacuo to obtain 85 g of escitalopram pamoate sample.

Example 4: Preparation of Escitalopram Pamoate 400 ml of water was added to 50 g of escitalopram oxalate sample, and was heated to 55° C. to completely dissolve it. 500 ml of water was added to 52 g of pamoate disodium salt to completely dissolve it at room temperature. The aqueous solution of pamoate disodium salt was added dropwise to the aqueous solution of escitalopram oxalate at 55° C., and a solid appeared immediately with being well dispersed. After the addition was completed, stirring was continued for 2 hours and then the reaction mixture was filtered. The filter cake was washed with 500 ml of water, filtered under vacuum for 10 min and dried in vacuo to obtain 85 g of escitalopram pamoate sample.

The above are only the preferred examples of the present invention, and are not intended to limit the present invention. Any modifications, equivalents, improvements, etc., which are made within the spirit and principles of the present invention, should be included in the scope of the present invention.

The invention claimed is:

1. A method for preparing a compound of formula I, comprising: dissolving escitalopram oxalate in a solvent and adding a pamoate aqueous solution dropwise to precipitate solids to obtain the compound of formula I,

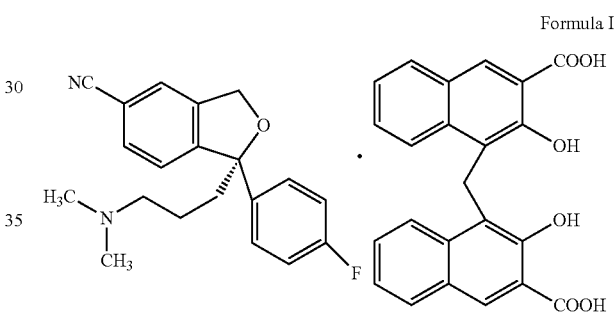

Formula I wherein the solvent is water.

2. The method according to claim 1, wherein dissolving is carried out at a temperature of 0-70° C.

3. The method according to claim 1 wherein dissolving is carried out at a temperature of 45-65° C.

4. The method according to claim 1, wherein the pamoate is a disodium pamoate salt.

5. The method according to claim 1, wherein adding the pamoate aqueous solution dropwise is carried out at a temperature of 0-70° C.

6. The method according to claim 1, wherein adding the pamoate aqueous solution dropwise is carried out at a temperature of 45-65° C.

* * * * *